(12) United States Patent
Kopke et al.

(10) Patent No.: US 9,289,404 B2
(45) Date of Patent: Mar. 22, 2016

(54) METHODS FOR TREATING BRAIN INJURY

(75) Inventors: Richard D. Kopke, Oklahoma City, OK (US); Robert A. Floyd, Oklahoma City, OK (US); Rheal Towner, Piedmont, OK (US)

(73) Assignees: HOUGH EAR INSTITUTE, Oklahoma City, OK (US); OKLAHOMA MEDICAL RESEARCH FOUNDATION, Oklahoma City, OK (US)

( * ) Notice: Subject to any disclaimer, the term of this patent is extended or adjusted under 35 U.S.C. 154(b) by 0 days.

(21) Appl. No.: 13/983,515

(22) PCT Filed: Feb. 3, 2012

(86) PCT No.: PCT/US2012/023855
§ 371 (c)(1),
(2), (4) Date: Aug. 2, 2013

(87) PCT Pub. No.: WO2012/106654
PCT Pub. Date: Aug. 9, 2012

(65) Prior Publication Data
US 2014/0187631 A1    Jul. 3, 2014

Related U.S. Application Data

(60) Provisional application No. 61/439,671, filed on Feb. 4, 2011.

(51) Int. Cl.
| | |
|---|---|
| A61K 31/185 | (2006.01) |
| A61K 31/198 | (2006.01) |
| A61K 31/221 | (2006.01) |
| A61K 31/15 | (2006.01) |
| A61K 31/205 | (2006.01) |
| A61K 38/06 | (2006.01) |
| A61K 31/16 | (2006.01) |
| A61K 31/555 | (2006.01) |
| A61K 38/07 | (2006.01) |

(52) U.S. Cl.
CPC ............... *A61K 31/185* (2013.01); *A61K 31/15* (2013.01); *A61K 31/16* (2013.01); *A61K 31/198* (2013.01); *A61K 31/205* (2013.01); *A61K 31/221* (2013.01); *A61K 31/555* (2013.01); *A61K 38/063* (2013.01); *A61K 38/07* (2013.01)

(58) Field of Classification Search
USPC ......................................... 514/547, 576, 562
See application file for complete search history.

(56) References Cited

U.S. PATENT DOCUMENTS

| | | |
|---|---|---|
| 5,508,305 A | 4/1996 | Carney |
| 5,780,510 A | 7/1998 | Carney |
| 2009/0234011 A1 | 9/2009 | Goldstein |
| 2010/0022458 A1 | 1/2010 | Kopke |
| 2010/0022661 A1 | 1/2010 | Lichter |
| 2010/0069309 A1 | 3/2010 | Gage |

FOREIGN PATENT DOCUMENTS

| | | |
|---|---|---|
| WO | WO 00/27376 | 5/2000 |
| WO | WO 01/28578 | 4/2001 |
| WO | WO 01/89407 | 11/2001 |
| WO | WO 2004/034999 | 4/2004 |
| WO | WO 2008/001386 | 1/2008 |

OTHER PUBLICATIONS

Fetoni (Protective effects of N-acetylcysteine on noiseinduced hearing loss in guinea pigs ACTA Ortorhinoloaryngologica Italica, 2009: 29 pp. 70-75).*
Lees (NSY-059 FOR Acute Ischemic Stroke, the New England Journal of Medicine, 354:6, 2006, pp. 588-600).*
Tyurin(Oxidative Stress Following Traumatic Brain Injury in Rats: Quantitation of Biomarkers and Detection of Free Radical Intermediates, Journal of Neurochemistry, 2000, vol. 75, No. 5, pp. 2178-2189).*
Ozkul (Oxidative stress in acute ischemic stroke, Journal of clinical Neuroscience, 2007, 14, pp. 1062-1066).*
Hans-Christoph Diener, et al., Stroke, Journal of the American Heart Association, Mar. 27, 2008, The American Heart Association, Dallas, TX, USA; (http://stroke.ahajournals.org/cgi/content/full/39/6/1751).
Eghwrudjakpor P O, et al., Oxidative Stress Following Traumatic Brain Injury: Enhancement of Endogenous Antioxidant Defence Systems and the Promise of Improved Outcome; Nig J Med 2010; 14-21; vol. 19, No. 1 Jan.-Mar. 2010.

* cited by examiner

*Primary Examiner* — Kathrien Cruz

(57) ABSTRACT

The treatment options for treating blast-induced and noise-induced traumatic brain injury and tinnitus are limited. Thus, the current invention provides methods for treating traumatic brain injury and tinnitus. The methods involve administering a pharmaceutically effective amount of a composition comprises 2,4-disulfonyl α-phenyl tertiary butyl nitrone and N-acetylcysteine (NAC).

11 Claims, 20 Drawing Sheets

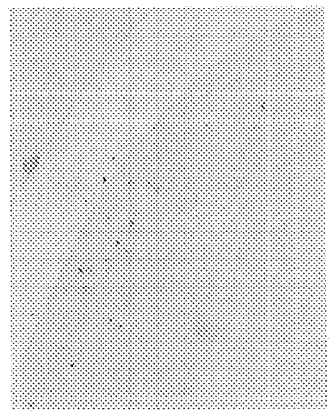
FIG. 1C
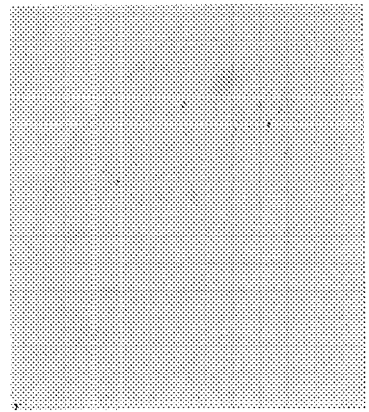
FIG. 1F
FIG. 1B
FIG. 1E
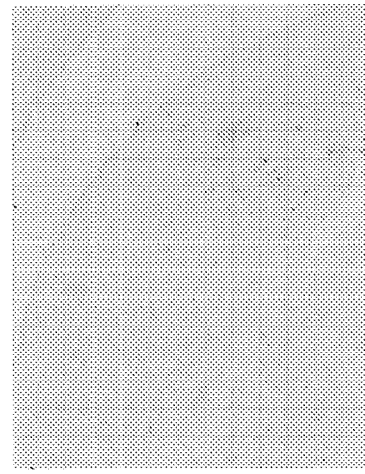
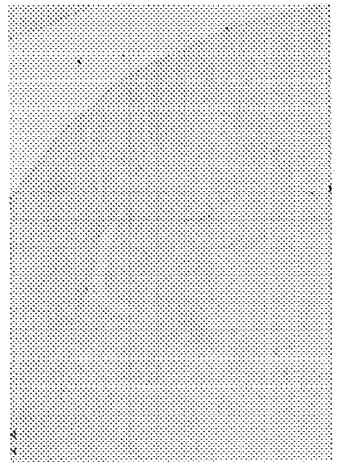
FIG. 1A
FIG. 1D

Fig. 8A
Fig. 8B
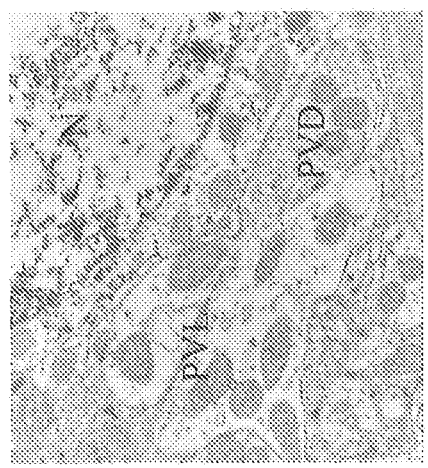
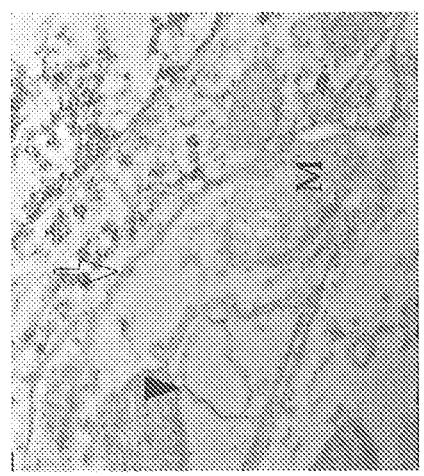
Fig. 8C
Fig. 8D
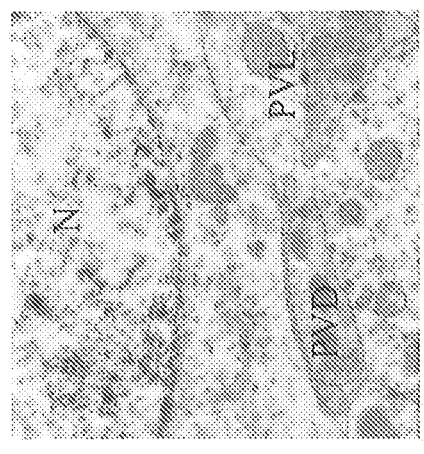
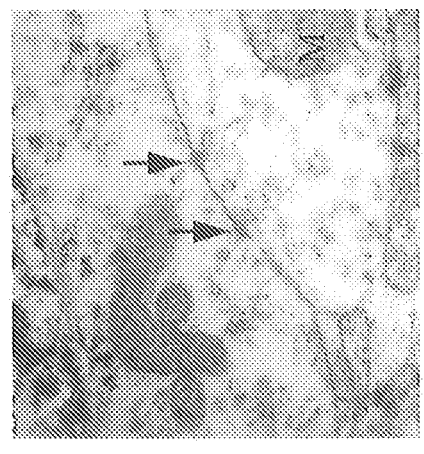
Fig. 8E
Fig. 8F

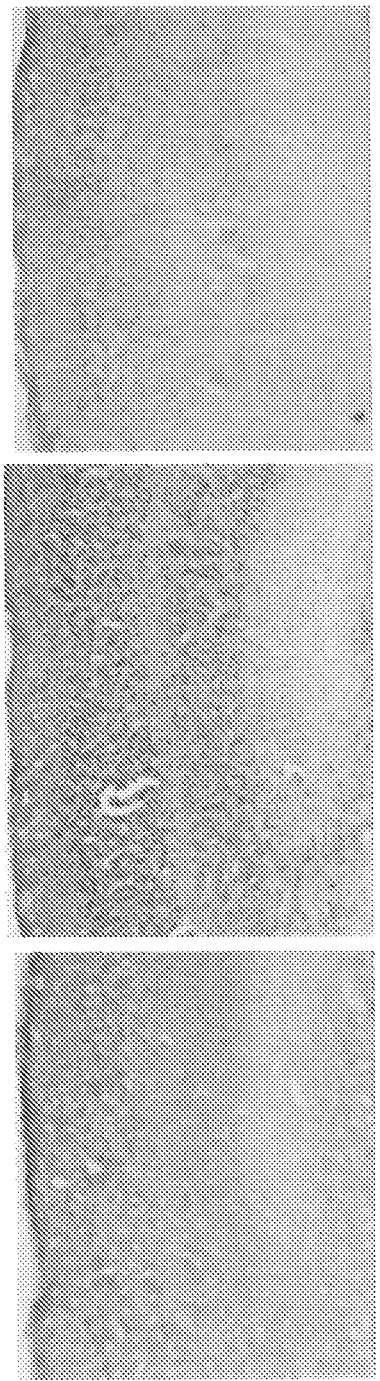
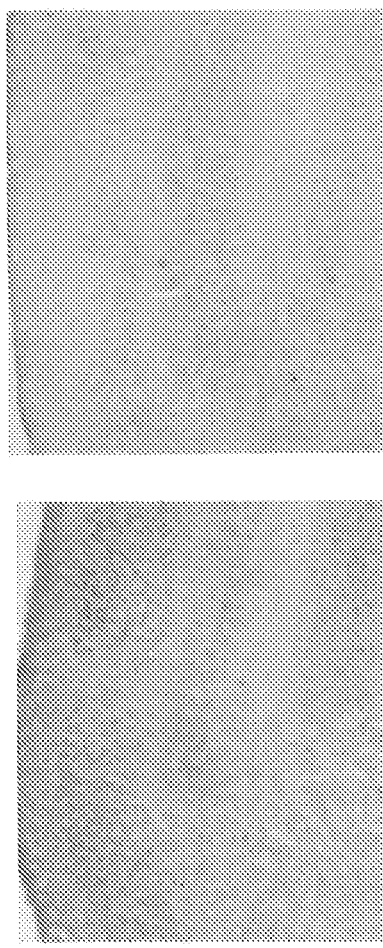
Fig. 13A  Fig. 13B  Fig. 13C  Fig. 13D  Fig. 13E

METHODS FOR TREATING BRAIN INJURY

CROSS RELATED

This application claims the benefit of previously filed International Application PCT/US12/023855 filed Feb. 3, 2012, and U.S. Provisional Application Ser. No. 61/439,671 filed Feb. 4, 2011.

BACKGROUND

There is increased evidence that blast overpressure is transmitted across the skull into the brain. This sets up the potential to cause traumatic brain injury (TBI) including damage to the central auditory centers of the brain, e.g. brainstem, temporal lobe, and thalamus which could explain symptoms such as hearing loss, dizziness, and tinnitus. Of particular significance is the observation that blast-related TBI produces significantly greater rates of hearing loss and tinnitus (60%) compared with non-blast related TBI. Similarly, intense sound- or noise-induced changes in the central auditory structure have been reported, including the cochlear nucleus, inferior colliculus, medial geniculate body and primary auditory cortex.

Although, some mechanical damage will have permanent effects, much of the long-term damage results from secondary molecular and cellular processes that are triggered by the blast-induced trauma amplify the effects of mechanical damage. TBI initiates an almost immediate injury process including contusion, diffuse axonal injury, hematoma, subarachnoid hemorrhage followed shortly thereafter by a variety of secondary injuries. The secondary injuries can include ischemia, edema, oxidative damage, decreased ATP, cytoskeleton changes, inflammation, and activation of cell death pathways. To date, an effective therapeutic approach that addresses these secondary molecular and cellular processes has yet to be thoroughly investigated. Thus, a substantial need exists for treatment methods and compounds suitable for treating these issues associated with victims of TBI.

SUMMARY

A method for treating noise-induced and blast-induced traumatic brain injury is provided. In one embodiment, a pharmaceutically effective amount of a composition comprising 2,4-disulfonyl α-phenyl tertiary butyl nitrone is administered to an organism that has suffered noise-induced or blast-induced brain injury. In one aspect of the current embodiment, the composition further comprises N-acetylcysteine (NAC). In another aspect of the current embodiment, the composition is administered orally.

A method for treating traumatic brain injury is provided. In one embodiment, a pharmaceutically effective amount of a composition comprising 2,4-disulfonyl α-phenyl tertiary butyl nitrone is administered to an organism that has suffered traumatic brain injury. In one aspect of the current embodiment, the composition further comprises N-acetylcysteine (NAC). In another aspect of the current embodiment, the composition is administered orally.

In another embodiment, the method for treating brain injury comprises administering a composition to an organism that has suffered a brain injury, wherein the composition comprises 4-hydroxy-α-phenyl butyl nitrone. In one aspect of this embodiment, the composition further comprises NAC. In another aspect of the current embodiment, the composition further comprises NAC and Acetyl-L-Carnitine (ALCAR). In yet another aspect of the current embodiment, the composition is administered orally.

A method for treating tinnitus is provided. In one embodiment, a pharmaceutically effective amount of a composition comprising 2,4-disulfonyl α-phenyl tertiary butyl nitrone is administered to an organism that is suffering from noise-induced tinnitus. In one aspect of the current embodiment, the composition further comprises N-acetylcysteine (NAC). In another aspect of the current embodiment, the composition is administered orally.

In another embodiment, the method for treating noise-induced tinnitus comprises administering a composition to an organism that is suffering from noise-induced tinnitus, wherein the composition comprises 4-hydroxy-α-phenyl butyl nitrone. In one aspect of this embodiment, the composition further comprises NAC. In another aspect of the current embodiment, the composition further comprises NAC and Acetyl-L-Carnitine (ALCAR). In yet another aspect of the current embodiment, the composition is administered orally.

The current invention also relates to a method for increasing the bioavailability of a compound in the central nervous system. The method involves administering 2,4-disulfonyl phenyl tertiary butyl nitrone to an organism in an amount sufficient to increase blood-brain barrier permeability and administering the compound to the organism either concurrently or following administration of 2,4-disulfonyl α-phenyl tertiary butyl nitrone.

BRIEF DESCRIPTION OF THE DRAWINGS

FIGS. 1A-1F provide images of the dorsal cochlear nucleus (DCN) immunostained for c-fos in control subjects (1A), subjects exposed to noise (1B—1 hour post noise; 1C—8 hours post noise; 1E—24 hours post noise), and subjects treated with 2,4-disulfonyl α-phenyl tertiary butyl nitrone (2,4-disulfonyl PBN) and NAC 4 hours after noise exposure (1D—8 hours post noise; 1F—24 hours post noise).

FIGS. 8A-8C provide transmission electron microscopic images of nerve terminals surrounding cartwheel cell bodies in the middle region of the DCN of control subjects (8A), subjects following noise exposure (8B) and subjects treated with 4-OHPBN+NAC+ALCAR four hours following noise exposure (8C).

FIGS. 8D-8F represent FIGS. 8A-8C, respectively, at a higher magnification.

FIGS. 13A-13E represent doublecortin immunostained sections of the entorhinal cortex in control subjects note exposed to noise trauma (FIG. 13A), subjects 21 days and 6 months post noise exposure without treatment (FIGS. 13B and 13D, respectively), and with HPN-07 treatment at the same time points (FIGS. 13C and 13E, respectively).

DETAILED DESCRIPTION

Figure 1G:
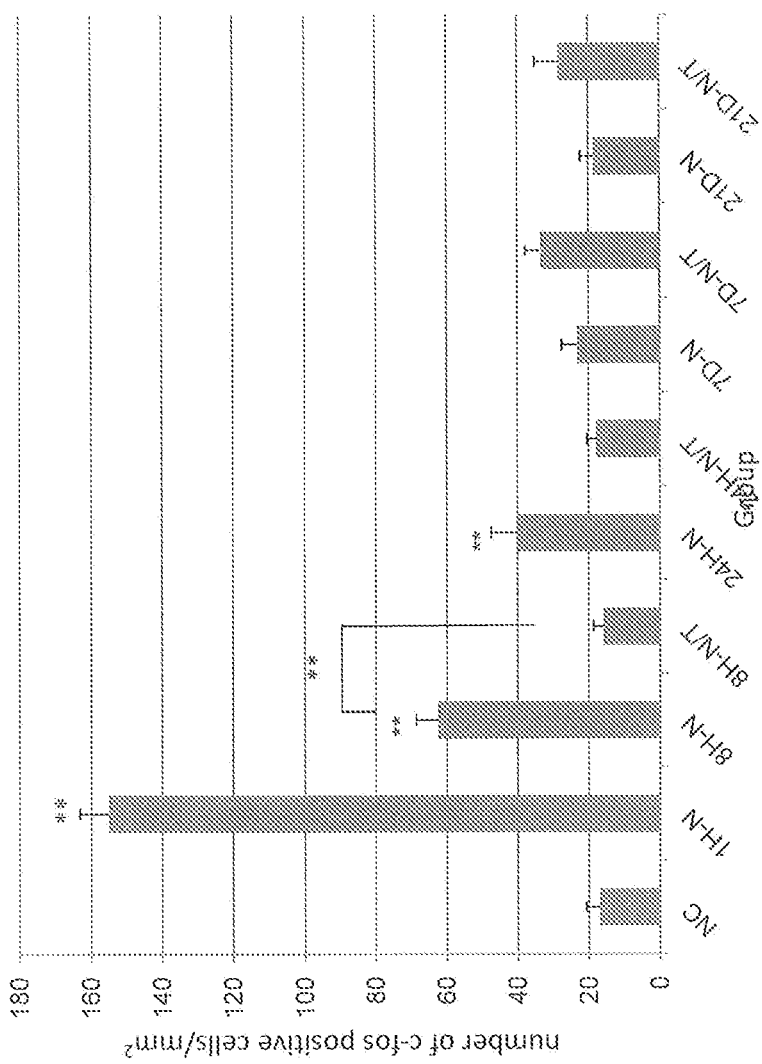
FIG. 1G provides a bar graph representing the number of c-fos positive cells counted in the DCN from the images of FIG. 1A-1F, where NC=normal controls, H-N=hours post noise exposure, D-N=days post noise exposure, and T=received treatment of 2,4-disulfonyl PBN+NAC.

The invention provides methods for treating noise-induced tinnitus and traumatic brain injury as well as brain injury related to oxidative stress, programmed cell death, or inflammatory processes. Traumatic brain injury (TBI) is an alteration in brain function, or other evidence of brain pathology, caused by an external force. The external forces causing the TBI include, but are not limited penetrating injuries (penetration of an object into the brain) and non-penetrating or closed injuries such as exposure to blasts or pressure (blast-induced TBI), head being struck by an object, or from exposure to noise (noise-induced TBI) The current invention demonstrates the functionality of 2,4-disulfonyl α-phenyl tertiary butyl nitrone and the synergistic effect of combining the 2,4-disulfonyl α-phenyl tertiary butyl nitrone with N-acetylcysteine (NAC) in the treatment of tinnitus and traumatic brain injury. For the purposes of the remainder of this disclosure, 2,4-disulfonyl α-phenyl tertiary butyl nitrone will be referred to as 2,4-disulfonyl PBN or HPN-07.

The 2,4-disulfonyl PBN has the following structure:

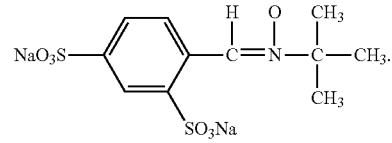

The acid form of the compound has the following structure:

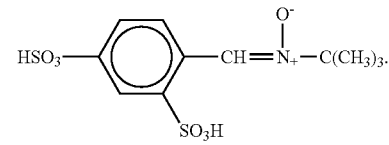

The acid form may be a solid or found in low pH solutions. The ionized salt form of the compound exists at higher pH and may be represented by either of the following structures:

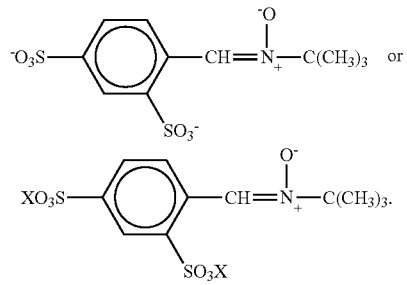

In the salt form, X is a pharmaceutically acceptable cation. Most commonly, this cation is a monovalent material such as sodium, potassium or ammonium, but it can also be a multivalent alone or cation in combination with a pharmaceutically acceptable monovalent anion, for example calcium with a chloride, bromide, iodide, hydroxyl, nitrate, sulfonate, acetate, tartrate, oxalate, succinate, palmoate or the like anion; magnesium with such anions; zinc with such anions or the like. Among these materials, the free acid and the simple sodium, potassium or ammonium salts are most preferred with the calcium and magnesium salts also being preferred but somewhat less so. The 2,4-disulfonyl PBN compound is described in detail by U.S. Pat. No. 5,488,145. The entire disclosure of U.S. Pat. No. 5,488,145 is incorporated herein by reference. The salts of 2,4-disulfonyl PBN may also be used for the treatment of brain injury and tinnitus in a manner similar to the use of 2,4-disulfonyl PBN as discussed below.

Additionally, antioxidant peptides, which target the mitochondria, are useful in the present invention and may be included as part of the composition for treating tinnitus and traumatic brain injury. These compounds preclude the generation of intracellular reactive oxygen species (ROS) which leads to oxidative stress and damage of the mitochondria. Oxidative damage of the mitochondria is known to cause apoptosis and necrosis leading to cell death. The preferred antioxidant peptides are Szeto-Schiller (SS) peptides and their functional analogs. These compounds have alternating aromatic residues and basic amino acids. In particular, peptides having tyrosine (Tyr) or dimethyltyrosine (Dmt) analogs can scavenge oxyradicals. These compounds inhibit oxidation of low-density lipoproteins. SS-peptides include compounds such as SS-31 (D-Arg-Dmt-Lys-Phe-$NH_2$) and SS-02 (Dmt-D-Arg-Phe-Lys-$NH_2$). In addition to the Tyr and Dmt containing SS-peptides, tryptophan containing SS-peptides are also useful in the current invention. Finally, the amino acids found in the SS-peptides may be L or D and may be naturally occurring, non-naturally occurring and derivatives of naturally occurring amino acids. In particular, the SS-peptides disclosed in PCT published application WO 2005/072295 are suitable for use in the current invention. The entire disclosure of WO 2005/072295, published on Aug. 11, 2005 is incorporated herein by reference. The composition of the current invention may optionally include antioxidant compounds including, but not limited to, Acetyl-L-Carnitine (ALCAR), glutathione monoethylester, ebselen, D-methionine.

In another embodiment, the current invention utilizes 4-hydroxy-α-phenyl butyl nitrone (4-OHPBN) or a derivative of 4-OHPBN alone or in combination with at least one antioxidant to treat brain injury and noise-induced tinnitus. Additionally, the derivatives of the 4-OHPBN may be formulated to enhance oral absorbtion, alter bioavailability kinetics, and/or formulated in a combination with one or more of the above compounds. Preferably, the compositions for treating brain injury and tinnitus will be administered orally. However, other methods which deliver the compositions systemically to the body should work equally well.

As demonstrated in the Examples, the inventors have discovered that 4-hydroxy-α-phenyl butyl nitrone (4-OHPBN) or 2,4-disulfonyl PBN, administered in combination with N-acetylcysteine (NAC) one to four hours after noise exposure or blast exposure can prevent molecular changes associated with the resulting traumatic brain injury. Furthermore, the areas of the brain affected by the noise or blast exposure, such as the dorsal cochlear nucleus, have been associated with the etiology of tinnitus thereby providing a novel therapeutic approach to treatment of tinnitus.

Although the preferred embodiments of the current invention are described primarily with respect to noise-induced tinnitus and noise-induced and blast-induced tramautic brain injury, it should be appreciated that the methods and compositions described herein may be used to treat traumatic brain injury and tinnitus caused by a variety of different events or factors. The methods described herein may be specifically useful in treating secondary injuries resulting from TBI including ischemia, edema, oxidative damage, decreased ATP, cytoskeleton changes, inflammation, and activation of cell death pathways.

The compositions of the current invention will preferably be administered orally; however, other delivery methods including, but not limited to, intravenously, subcutaneously, by inhalation, sublingually, subdermally or intrathecally. Further the active composition may be administered as a nanoparticle or dendrimer formulation. The nanoparticle may be multifunctional and composed of a polymer and paramagnetic iron oxide particles to allow the application of external magnetic forces to aid in the delivery of the drug to the desired target such as the dorsal cochlear nucleus. Additionally, the composition may be formulated with additives known to those skilled in the art to enhance oral absorbtion and alter bioavailability kinetics.

EXAMPLES

In the examples to follow, the inventors demonstrate that exposure to high levels of noise and blasts (high pressure exposure) can induce molecular and cellular changes associated with traumatic brain injury in the certain regions including the dorsal cochlear nucleus, the hippocampus, and the entorhinal cortex. Moreover, the inventors demonstrate that administration of a composition comprising 2,4-disulfonyl PBN (HPN-07) either alone or in combination with NAC can reverse the cellular changes associated with the traumatic brain injury. In doing so, symptoms of the traumatic brain injury, including noise-induced tinnitus can be lessened. Alternatively, the inventors demonstrate that a composition comprising 4-hydroxy-α-phenyl butyl nitrone, NAC and ALCAR can have similar therapeutic effects.

Example 1

The purpose of this example is to demonstrate that a composition comprising 2,4-disulfonyl PBN (HPN-07) and NAC is effective in reversing molecular changes indicative of noise-induced traumatic brain injury in the dorsal cochlear nucleus.

MRI studies of animals experiencing chronic acoustic exposure-induced tinnitus have demonstrated increased brain activity in the dorsal cochlear nucleus. Expression of c-fos, an immediate-early gene, is widely used as an accepted marker of neuronal activity. Increases in c-fos expression have been observed in the central nerve system few hours to 5.5 weeks after noise exposure suggesting that c-fos expression might represent a neural correlate of tinnitus or of plasticity associated with noise induced tinnitus. Increased expression of c-fos has also been associated with brain injury. In the present example, c-fos expression was examined 1 hours to 21 days following 115 dB SPL octave-band noise exposure both with and without administration of a composition comprising HPN-07 and NAC.

Adult rats (Spraue Dawley, 4-6 in each group) were used in the study. The animals in the noise groups (N) and the noise plus treatment groups (N/T) were exposed to 115 dB SPL octave-band noise centered at 14 kHz for 1 hour. A composition comprising 20 mg/kg HPN07 and 50 mg/kg NAC was intraperitoneally administrated 4 hours after the noise exposure and twice a day for the next 2 days. Rats receiving no noise exposure served as normal controls (NC). Auditory brainstem response (ABR) and distortion product otoacoustic emission (DPOAE) were recorded before noise exposure and euthanasia. Brainstems were harvested 1 hour (1 H), 8 H, 24 H, 7 days (7 D) and 21 D after noise exposure and processed for paraffin embedding and sectioning at a thickness of 6 μm. Cells positive for c-fos were identified in sections by immunohistochemical staining. Immuno-density was determined by light microscopy as the number of positive cells per sq. mm. The data was analyzed statistically (oneway ANOVA and Tukey HSD tests).

FIG. 1. depicts examples of c-fos immunostaining images obtained from the dorsal cochlear nucleus (DCN) of the normal control (A), the noise exposure (B, C, E) and the noise/treatment (D, F) groups by light microscopy. Numerous positive c-fos stained cells were mainly found in the fusiform soma layer with few positive cells in the molecular and deep layers 1 H after noise exposure (B), suggesting that c-fos expression was up-regulated in the DCN immediately after noise exposure. The number of positive cell decreased 8 H (C) and 24 H (E), and returned to the normal lever 7 D and 21 D (not shown) after noise exposure. Positive stained cells in the DCN were counted and statistically analyzed (G). A significant increased number of c-fos positive cells were found in the 1 H-N, 8 H-N and 24 H-N groups compared to the NC group (p<0.01). A significant difference was also found between the 8 H-N and 8 H-N/T groups (p<0.01), suggesting that treatment with a composition comprising HPN-07 and NAC down-regulates c-fos expression in the DCN at this time point after noise exposure.

Figure 2:
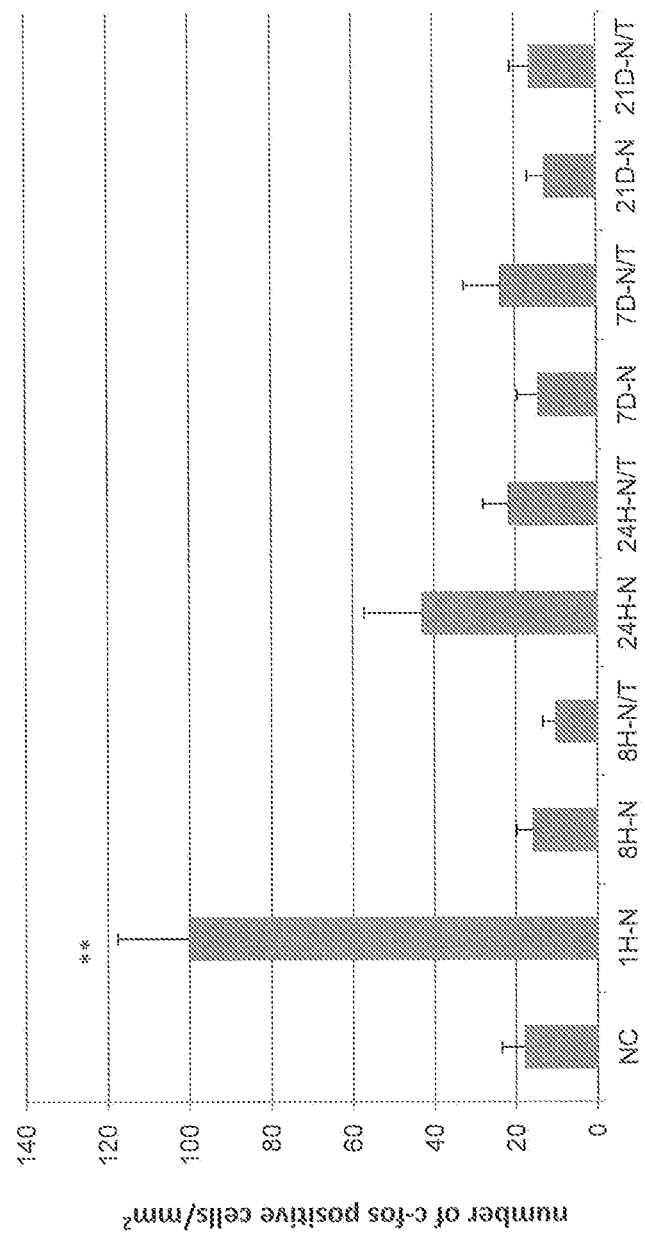
FIG. 2 provides a bar graph representing the number of c-fos positive cells in the posteroventral cochlear nucleus (PVCN) at various time points post noise exposure in the absence and presence of treatment with 2,4-disulfonyl PBN) and NAC, where NC=normal controls, H-N=hours post noise exposure, D-N=days post noise exposure, and T=received treatment of 2,4-disulfonyl PBN+NAC.
Figure 3C:
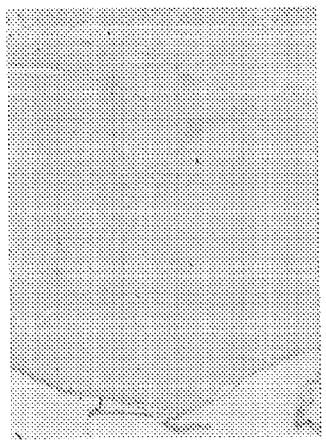
FIGS. 3A-3F provide images of the anteroventral cochlear nucleus. (AVCN) immunostained for c-fos in control subjects (3A), subjects exposed to noise (3B—1 hour post noise; 3C—8 hours post noise; 3E—24 hours post noise), and subjects treated with 2,4-disulfonyl PBN and NAC 4 hours after noise exposure (3D—8 hours post noise; 3F—24 hours post noise).
Figure 3F:
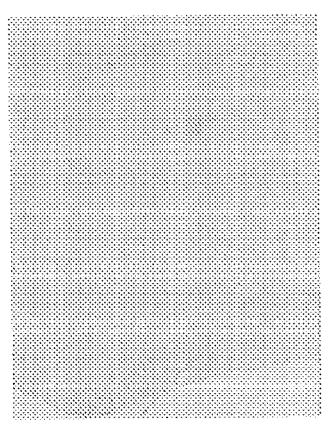
Figure 3B:
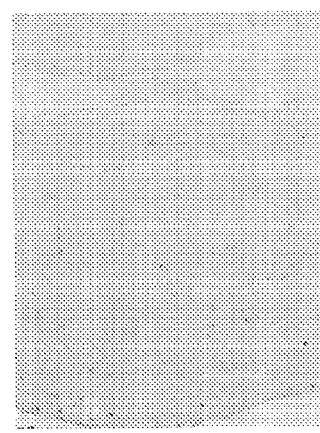
Figure 3E:
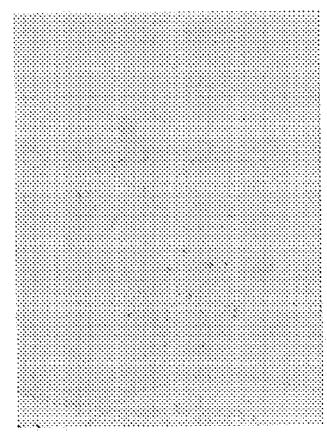
Figure 3A:
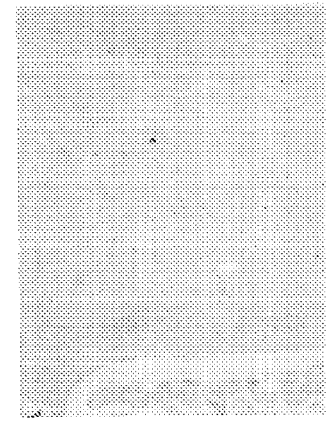
Figure 3D:
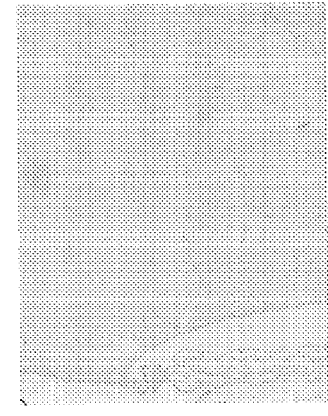
Figure 3G:
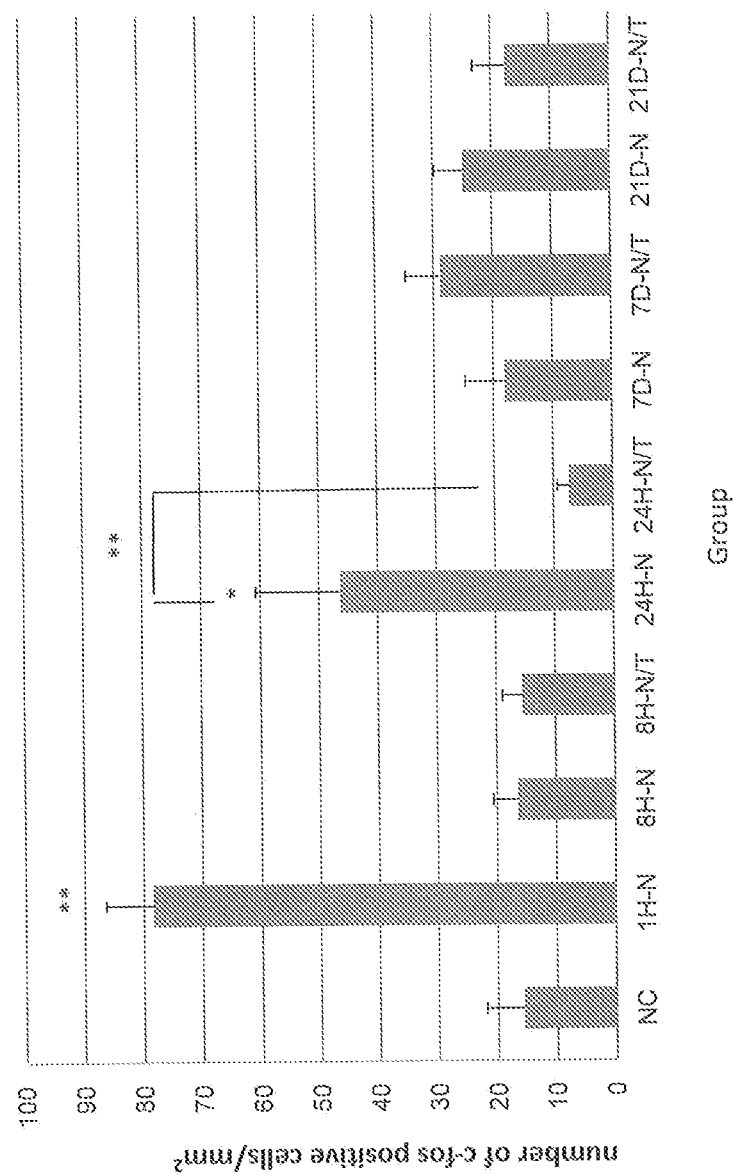
FIG. 3G provides a bar graph representing the number of c-fos positive cells counted in the AVCN from the images of FIG. 3A-3F, where NC=normal controls, H-N=hours post noise exposure, D-N=days post noise exposure, and T=received treatment of 2,4-disulfonyl PBN+NAC.

FIG. 2 depicts the results of c-fos immunostaining density measurement in the PVCN. A significant increased number of c-fos positive cells were found in the 1 H-N group compared to the NC group (p<0.01), suggesting that c-fos expression was up-regulated in the PVCN immediately after noise exposure.

FIG. 3 provides examples of c-fos immunostaining images obtained from the anteroventral cochlear nucleus (AVCN) of the normal control (A), the noise exposure (B, C, E) and the noise/treatment (D, F) groups by light microscopy. Many positive c-fos stained cells were found in the AVCN 1 H after noise exposure (B), suggesting that c-fos expression was up-regulated in the AVCN immediately after noise exposure. The number of positive cell returned to the normal level 8 H (C) and 7-21 D (not shown) after noise exposure. However, there was a second peak of up-regulation 24 H after noise exposure. Positive stained cells in the DCN were counted and statistically analyzed (G). A significant increased number of c-fos positive cells were found 1 H-N, and 24 H-N groups compared to the NC group (p<0.05 or 0.01). A significant difference was also found between the 8 H-N and 8 H-N/T groups (p<0.01), suggesting that administration of the composition comprising HPN-07+NAC down-regulated c-fos expression in the DCN at this time point after noise exposure.

Figure 4:
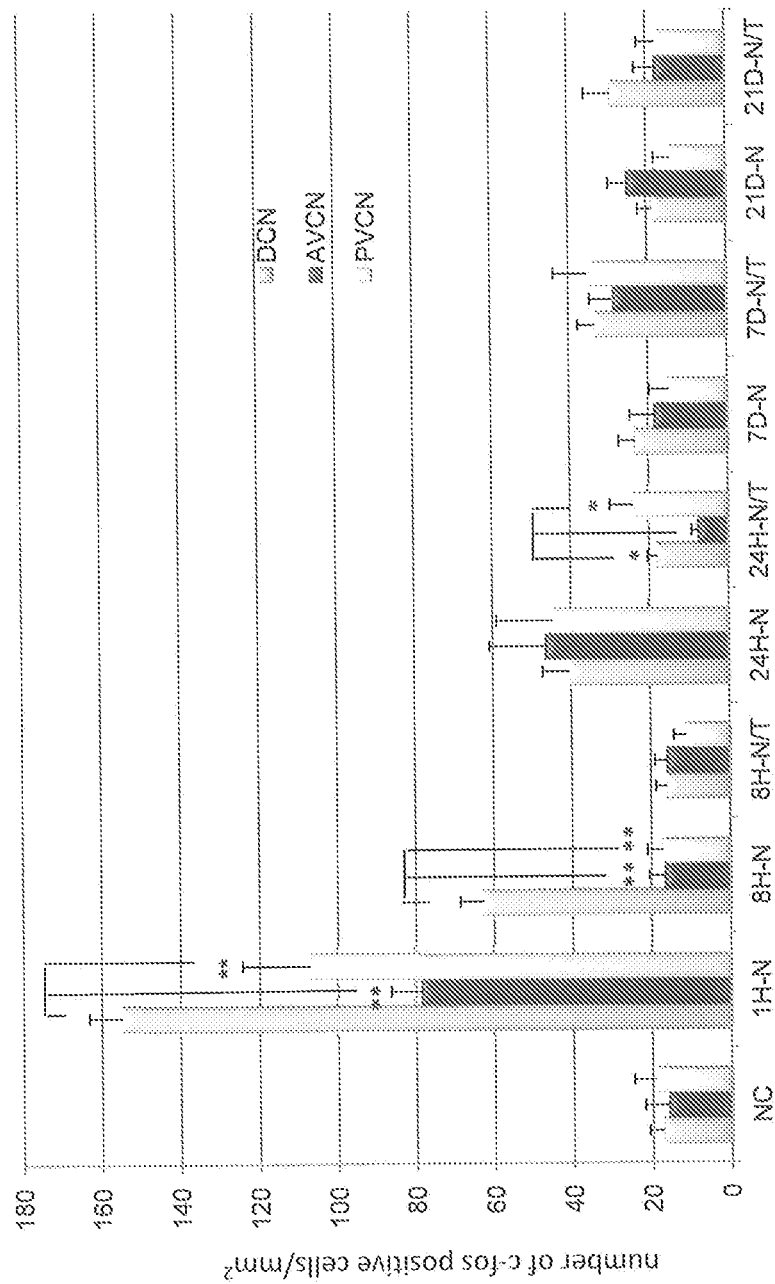
FIG. 4 provides a bar graph representing a comparison of the results from FIG. 1G, FIG. 2 and FIG. 3G.
Figure 5A:
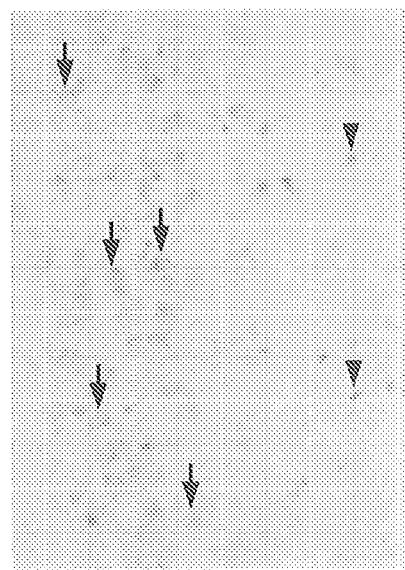
FIGS. 5A-5C provide images of the middle region of the DCN immunostained for precerebellin in control subjects (5A), subjects exposed to noise (5B), and subjects exposed noise and treatment with 4-hydroxy-α-phenyl butyl nitrone (4-OHPBN)+NAC+ALCAR (5C).
Figure 5B:
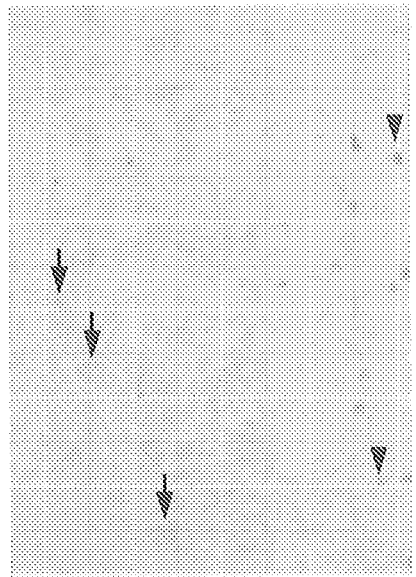
Figure 5C:
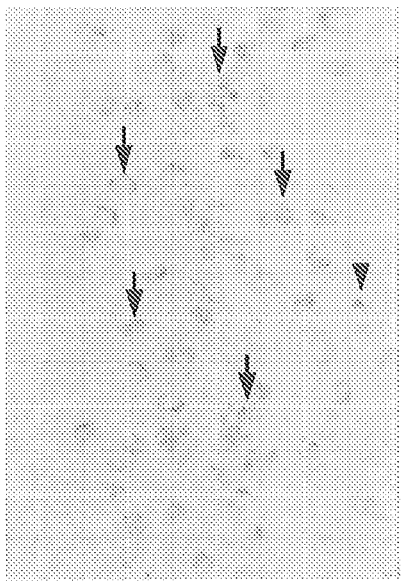
Figure 5D:
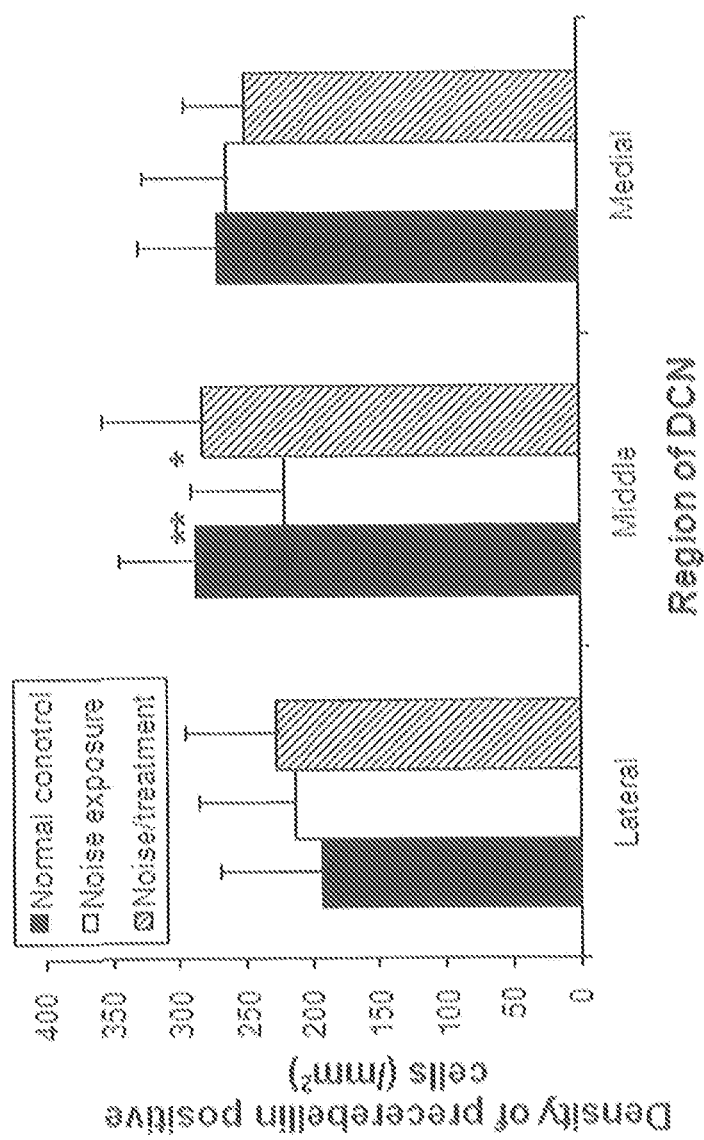
FIG. 5D provides a bar graph representing the density of precerebellin positive cells in the lateral, middle, and medial regions of the DCN in control subjects, subjects exposed to noise, and subjects exposed noise and treatment with 4-OHPBN+NAC+ALCAR.
Figure 6A:
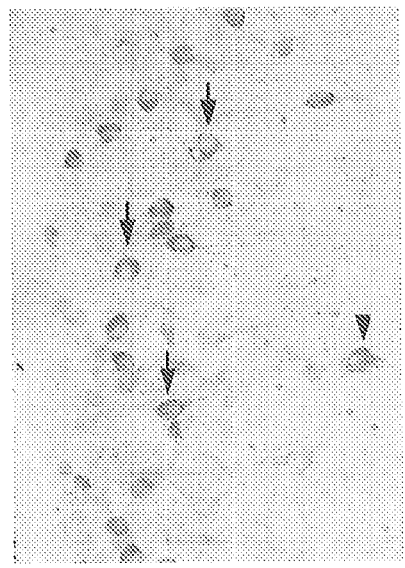
FIGS. 6A-6C provide images of the middle region of the DCN immunostained for PEP-19 in control subjects (6A), subjects exposed to noise (6B), and subjects exposed noise and treatment (4-OHPBN+NAC+ALCAR) (6C).
Figure 6B:
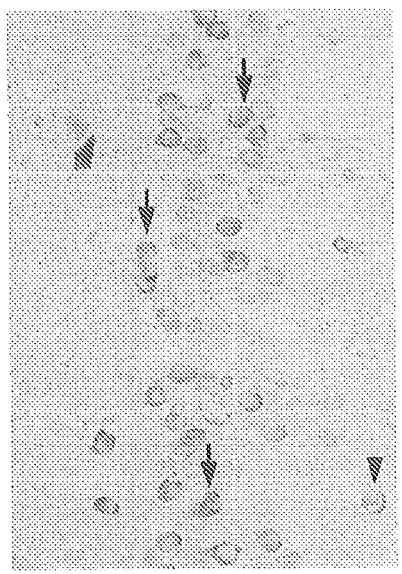
Figure 6C:
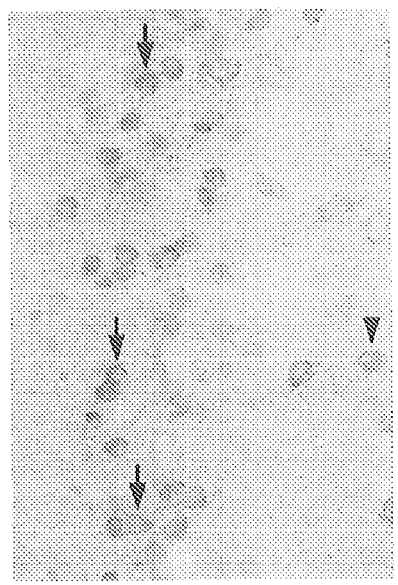
Figure 6D:
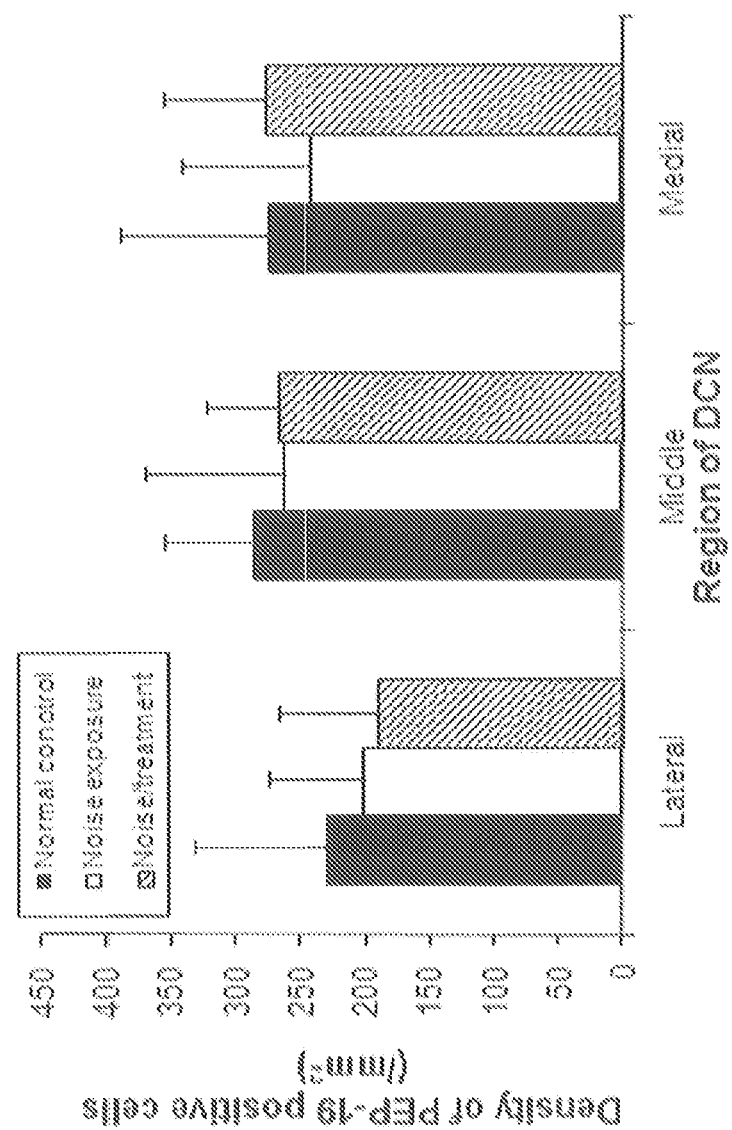
FIG. 6D provides a bar graph representing the density of PEP-19 positive cells in the lateral, middle, and medial regions of the DCN in control subjects, subjects exposed to noise, and subjects exposed noise and treatment (4-OHPBN+NAC+ALCAR).
Figure 7B:
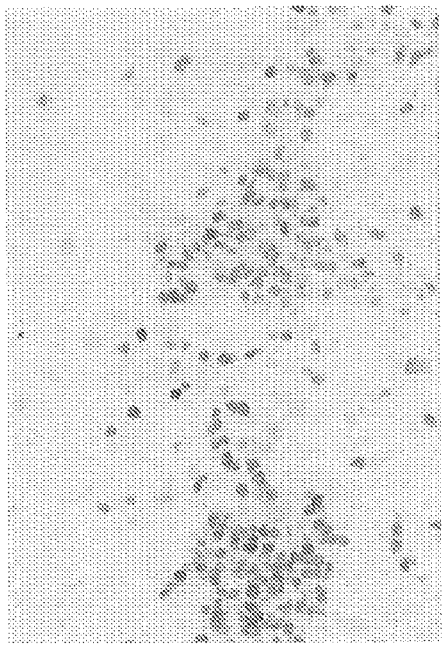
FIGS. 7A-7C provide images of the middle region of the DCN immunostained for NeuN in control subjects (7A), subjects exposed to noise (7B), and subjects exposed noise and treatment (4-OHPBN+NAC+ALCAR) (7C).
Figure 7C:
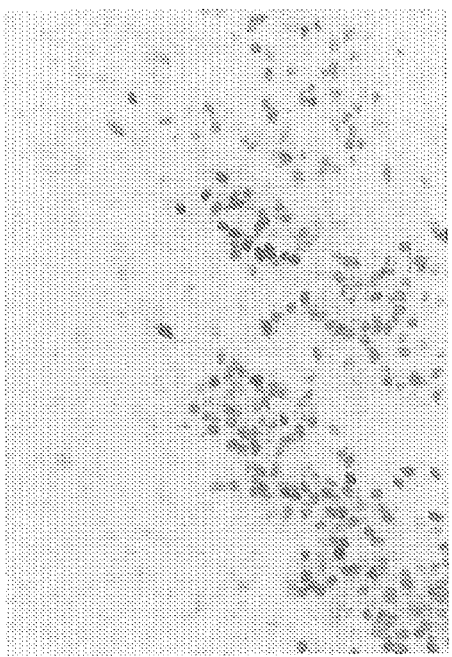
Figure 7A:
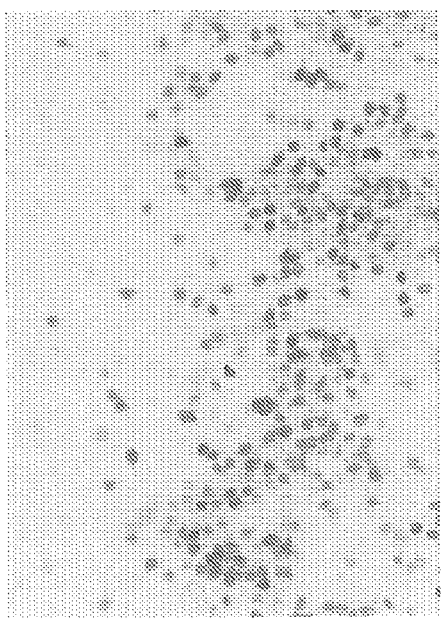
Figure 7D:
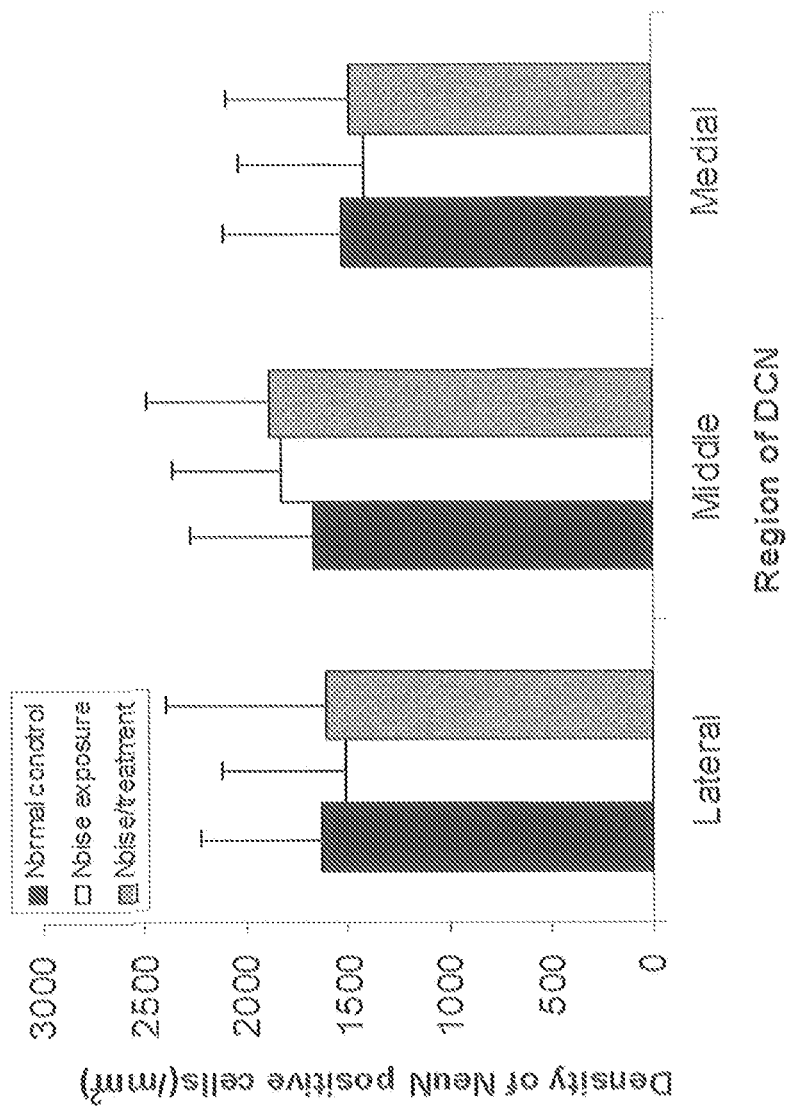
FIG. 7D provides a bar graph representing the density of Neu-N positive cells in the lateral, middle, and medial regions of the DCN in control subjects, subjects exposed to noise, and subjects exposed noise and treatment (4-OHPBN+NAC+ALCAR).
Figure 8G:
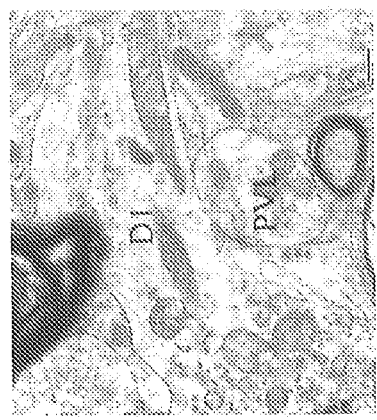
FIGS. 8G-8I provide transmission electron microscopic images of nerve terminals surrounding the primary dendrites of cartwheel cell bodies in the middle region of the DCN of control subjects (8G), subjects following noise exposure (8H) and subjects treated with 4-OHPBN+NAC+ALCAR four hours following noise exposure (8I).
Figure 8J:
FIGS. 8J-8L represent FIGS. 8G-8I, respectively, at a higher magnification.
Figure 8H:
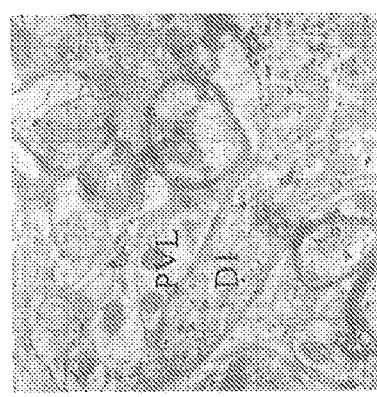
Figure 8K:
Figure 8I:
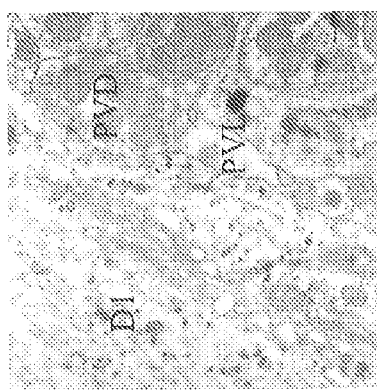
Figure 8L:
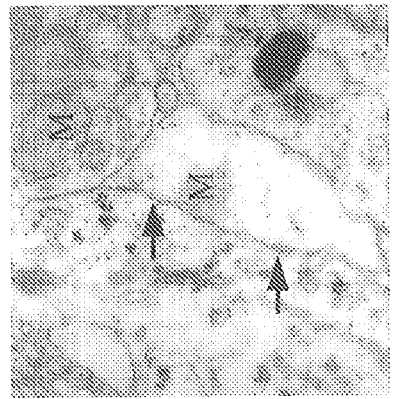

FIG. 4 provides a comparison of c-fos expression in the DCN, AVCN and PVCN at different time points after noise exposure and HPN-07+NAC treatment. Significant differences were found among three nuclei in 1 H-N, 8 H-N and 24 H-N/T groups (p<0.05 or 0.01). The DCN had significantly more c-fos positive cells than VCN at two time points (1 H and 8 H) after noise exposure (p<0.01), suggesting the DCN is also sensitive to noise exposure although it has direct auditory input only in its deep layer.

In sum, Example 1 demonstrates the following: (1) c-fos expression was up-regulated in neurons of the cochlear nucleus immediately after noise exposure; (2) c-fos expression returned to the normal level 24 hours after noise exposure in the DCN and 8 H in the VCN; (3) a second peak of up-regulation in the AVCN 24 H after noise exposure; (4) more c-fos positive neurons were found in the DCN than in the VCN after noise exposure; and (5) administration of a composition comprising HPN-07 and NAC can down-regulate c-fos expression in the DCN (8 H) and the AVCN (24 H). This data suggests that treatment with HPN-07 and NAC is effective in reducing the effects of noise-induced traumatic brain injury in the DCN and AVCN. Furthermore, animals with psychophysical evidence of noise-induced tinnitus have previously demonstrated elevated spontaneous activity in the DCN, suggesting that such hyperactivity may be related to the noise-induced tinnitus. Thus, these results also suggest that the combination of HPN-07 and NAC may be effective in treating noise-induced tinnitus and other conditions associated with noise-induced injury to the cochlear nucleus.

Example 2

In the present example, cell type specific synapse activity markers, precerebellin, and neuron markers, PEP-19 (cartwheel cell marker) and NeuN, as well as transmission electron microscopic studies (TEM) have been used to examine synaptic degeneration in the DCN of chinchilla 10 days after a 105 dB SPL octave-band noise exposure and in the absence and presence of a composition comprising 4-hydroxy-α-phenyl butyl nitrone, NAC and ALCAR (4-OHPBN+NAC+ALCAR) beginning 4 hours after noise exposure.

Three to five year old chinchilla were divided into 3 groups (6 in each group): 1) normal control; 2) noise exposure only (105 dB SPL octave-band noise centered at 4 kHz for 6 hrs); 3) noise exposure plus treatment with 4-OHPBN+NAC+ALCAR beginning 4 hours after noise exposure and twice a day for the next 2 days. Animals in the treatment group received 20 mg/kg of 4-OH-PBN dissolved in dimethyl sulfoxide (40%), polyethylene glycol 400 (40%), and saline (20%), 50 mg/kg of 20% NAC in water (containing 0.05% edetate disodium, dehydrate, PH 7.0, Hospira Inc., lake Forest, Ill.), and 20 mg/kg of ALCAR (Sigma-Aldrich Inc. St. Louis, Mo.) in saline. These agents were intraperitoneally administered separately. The brainstems were collected and fixed by 4% paraformaldehyde intracardial perfusion. The brainstems were serially sectioned with a cryotome at a thickness of 18-20 p.m. Immunohistochemical labeling using anti-precerebellin, anti-PEP-19, or anti-NeuN antibodies was carried out on the sections to evaluate the effectiveness of the treatment on synaptses and neurons after noise exposure. Immunodensity was measured as the number of immuno positive cells per square mm. Cell counts were analyzed statistically (oneway ANOVA and Tukey HSD tests). Brain tissue from three chinchilla (one for each group) perfused with 4% freshly depolymerized paraformaldehyde and 0.125% glutaradehyde were used for TEM study to examine synaptic degeneration in the middle region of the DCN of chinchilla.

FIG. 5 provides examples of precerebellin immunostaining images obtained from the middle region of the DCN of the normal control (5A), noise exposure (5B) and the noise/treatment (5C) groups by light microscopy. Positive precerebellin stained cells were found in the fusiform soma and deep layers of the DCN (arrows and arrowheads in A-C). Positive stained cells in the fusiform soma layer were counted and statistically analyzed (D). Significant differences were found among the groups only in the middle region of the DCN, but not in the lateral or medial regions. In the middle region, significant differences were found between the normal control and the noise exposure groups (p<0.01); as well as between the noise exposure and the noise/treatment groups (p<0.05).

FIG. 6 provides examples of PEP-19 immunostaining images obtained from the middle region of the DCN of the normal control (6A), the noise exposure (6B) and the noise/treatment (6C) groups by light microscopy. Positive PEP-19 stained cells were found in the fusiform soma and deep layers of the DCN (arrows and arrowheads in A-C). Positive stained cells in the fusiform soma layer were counted and statistically analyzed (D). No significant differences were found among the groups in all regions (p>0.05).

FIG. 7 provides examples of NeuN immunostaining images obtained from the middle region of the DCN of the normal control (7A), the noise exposure (7B) and the noise/treatment (7C) groups by light microscopy. Numerous positive NeuN stained cells were found in the fusiform soma and deep layers, and few in the molecular layer of the DCN. Positive stained cells were counted and statistically analyzed (D). No significant differences are found among the groups in all regions (p>0.05).

FIG. 8 provides examples of nerve terminals surrounding cartwheel cell bodies (A-F) and their primary dendrites (D1, G-L) in the middle region of the DCN of the normal control (left column), noise exposure (middle column) and noise/treatment (right column) chinchilla. The images in panels D-F and J-L are the higher magnification of the images in panels A-C and G-I, respectively. Two types of terminals, PVD (pleomorphic vesicles, dense) and PVL (pleomorphic vesicles, lucent), were found surrounding cartwheel cell bodies and their primary dendrites. No obvious changes were seen in the PVD synaptic terminals of all 3 groups of chinchilla. Compared to the PVL of the normal control group, huge vesicles were seen in the PVL of the noise exposure and the noise/treatment groups (arrowheads in E, F, K), but not in the PVL of the nerve terminals surrounding D1 of the noise/treatment group (L). Furthermore, the synaptic membranes which have a convex shape in the normal control and noise/treatment groups (arrows in D, F, J and L) appeared flattened and with a lower density contour in the noise exposure chinchilla (empty arrow in E and K).

In sum, example 2 demonstrates the following: (1) Downregulated expression of precerebellin was found only in the middle region of the DCN of the noise exposure group; (2) noise exposure used in the present study did not cause cartwheel cell loss (labeled by PEP-19) or other neuron loss (labeled by NeuN) in the DCN; (3) TEM showed enlarged vesicles and flattened synaptic membranes in the nerve terminals surrounding cartwheel cell bodies and their primary dendrites in the middle region of the DCN; (4) synapse degeneration in the middle region of the DCN is likely one of the results of noise exposure; and (5) administration of a composition comprising 4-OHPBN+NAC+ALCAR significantly restored precerebellin expression and decreased degeneration of synapses surrounding cartwheel cell body and their primary dendrites in the DCN. Thus, early treatment with 4-OHPBN+NAC+ALCAR following noise exposure acts to preserve normal central auditory structure.

Example 3

The purpose of this example is to demonstrate the effect of 2,4-disulfonyl PBN (HPN-07) in combination with NAC on various brain injury biomarkers in the hippocampus and cortex following blast exposure.

Male Long-Evans pigmented rats were exposed to 3 blasts (14 psi, 1.5-minute intervals between blasts). Rats were injected intraperitoneally with 300 mg/kg of NAC plus 300 mg/kg of HPN-07 in normal saline 1 hour after blast exposure and then continued twice a day for the following two days in the treatment group of rats. Rats with or without blast were injected carrier solutions and used as controls. Six rats were used in each group and each time point. All animals were intracardially perfused with 10% paraformaldehyde 3, 24 hours, 7 days and 21 days after blast (6 rats at each time point in each group, total 54 rats). Brains were collected and cryosectioned at 30 μm. Amyloid precursor protein (APP) and Glial Fibrillary Acidic Protein (GFAP) levels were measured in the CA1 region of the hipoocampus and auditory cortex to indicate the level of trauma or blast induced brain injury. The levels were measured by immunohistochemical staining using rabbit anti-APP IgG (1:100, Millipore), or GFAP IgG (1:500, Millipore) and Avidin Biotin Complex (ABC) Method. Images were collected by light or confocal microscopy. APP positive staining was counted and analyzed statistically (ANOVA and post hoc tests) as demonstrated in FIG. 9.

Figure 9:
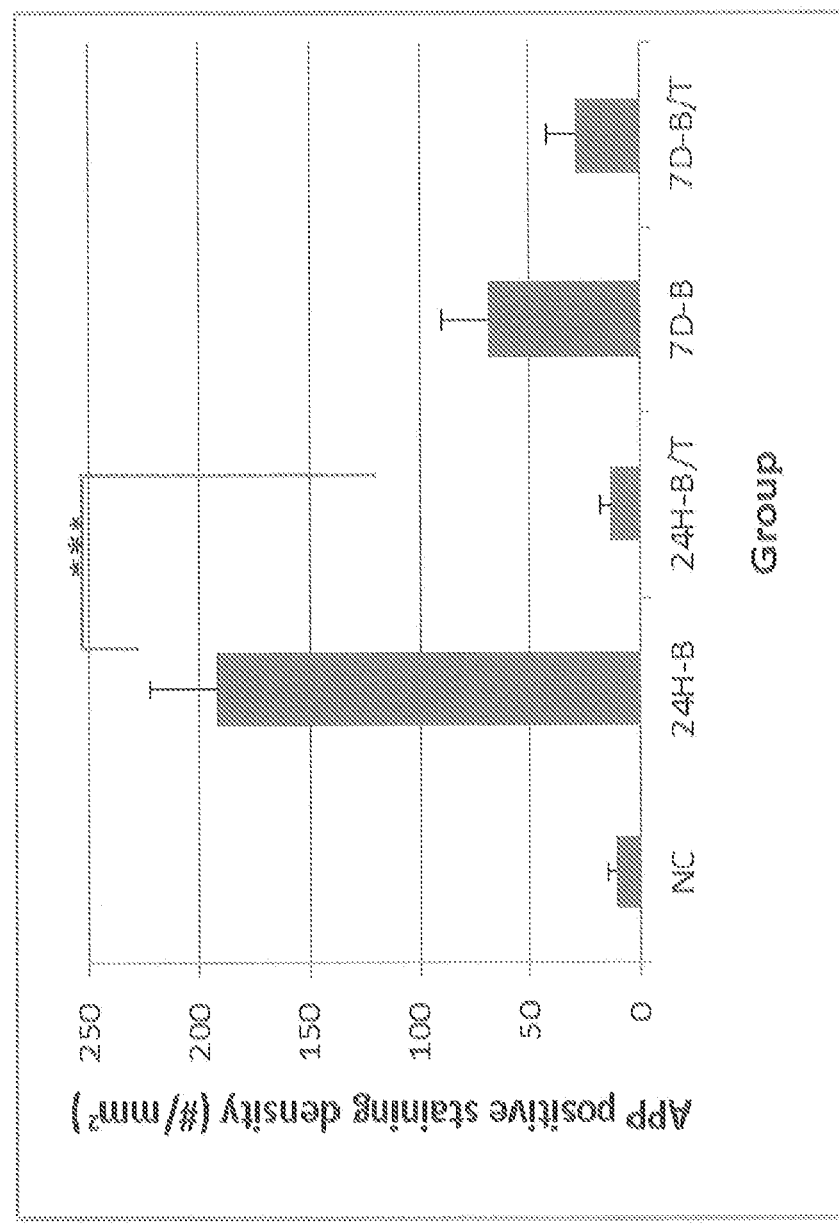
FIG. 9 provides a bar graph representing the density of cells positive for amyloid precursor protein (APP) in the hippocampus of subjects exposed to blast, where NC=normal controls (no blast), H-B=hours post blast, D-B=days post blast, and T=treatment with 2,4-disulfonyl PBN+NAC 4 hours post blast.
Figure 10A:
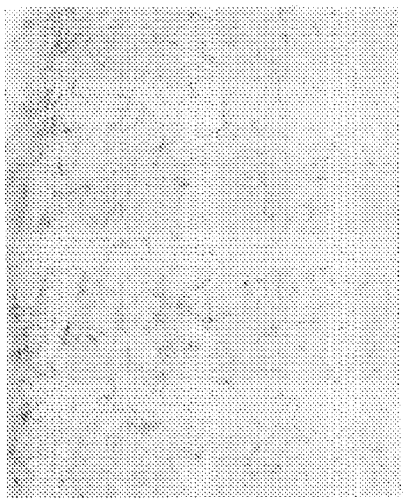
FIG. 10A provides a light microscopy image (4× magnification) of the DCN immunostained for glial fibrillary acidic protein (GFAP) in a normal control subject.
Figure 10B:
FIGS. 10B-10D provide light microscopy images (20× magnification) of the middle region of the DCN immunostained for GFAP of normal control subjects (10B), subjects exposed to blast (10C), and subjects exposed to blast followed by treatment with 2,4-disulfonyl PBN+NAC (10D).
Figure 10C:
Figure 10D:
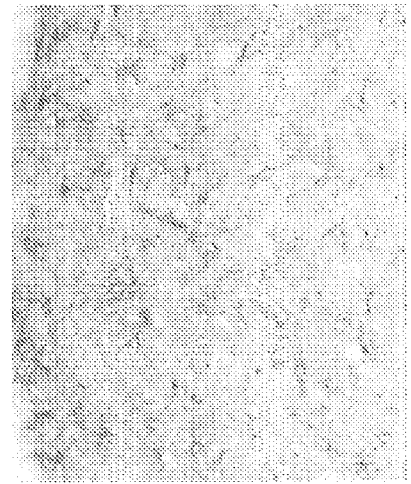
Figure 10E:
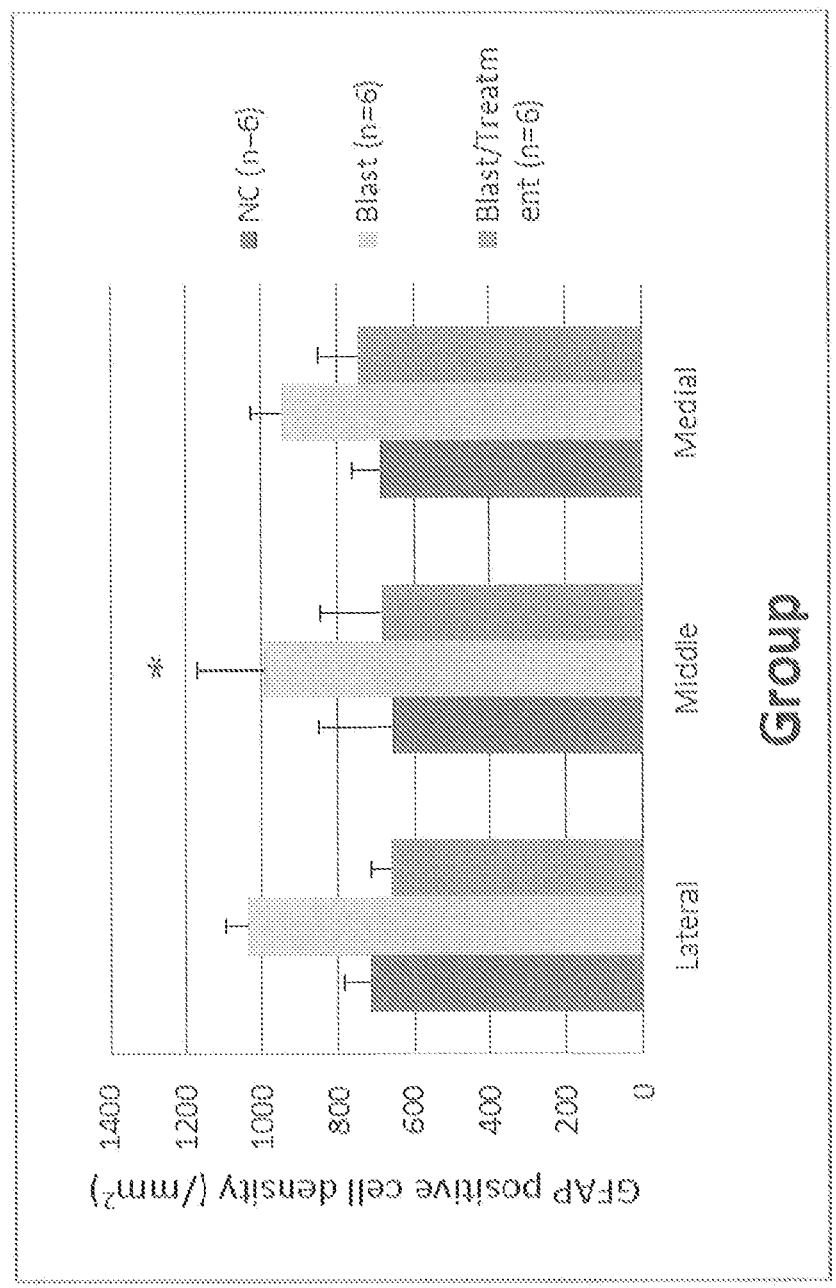
FIG. 10E provides a bar graph representing the density of GFAP positive cells in the lateral, middle, and medial regions of the DCN in control subjects, subjects exposed to blast, and subjects exposed to blast followed by treatment with 2,4-disulfonyl PBN+NAC.

APP staining is absent in the CA1 region of the hippocampus and cortex in the control group (no blast). However, 24 hours after exposure to blast, strong APP positive staining is found in the CA1 region of hippocampus and the cortex indicative of brain injury. This injury is decreased in both regions upon combination treatment with HPN-07 and NAC (confocal images not shown). It was also observed that APP protein accumulates in axons and cell bodies as a response to injury (confocal images not shown). FIG. 9 provides a quantification of the APP positive bodies found in the confocal images. A significant difference was found between normal control (NC) and blast groups (24 H-B) (P<0.001 and 0.05), as well as between blast (24 H-B) and blast plus treatment (24 H-B/T) 24 hours after blast (P<0.001). These results indicates that the combination of HPN-07 and NAC one hour after blast exposure inhibits APP formation and expression in brain thereby suggesting that damage resulting from blast-induced brain injury is reduced with HPN-07+NAC treatment.

FIG. 10 depicts GFAP immunostaining images obtained from the dorsal cochlear nucleus (DCN—4×, FIG. 10A) and the middle region of the DCN of the normal control (20×, FIG. 10B), the blast exposure (FIG. 10C) and the blast/treatment (FIG. 10D) groups by light microscopy 21 days after blast. Positive GFAP stained cells are found in the all layers of the DCN while most of them are located in the superficial layer. Few positive cells are found in the normal control. More GFAP positive cells are found in the DCN 21 days after blast and fewer positive cells are found in the DCN after treatment. Positively stained cells in the DCN were counted and statistically analyzed, and the results are provided in FIG. 10E. Significant differences were found between the groups in the middle region of the DCN (p<0.05), but not in the lateral and medial regions of the DCN (all p>0.05). These results demonstrate that treatment with HPN-07 and NAC may inhibit glial activity after blast exposure with a regional effect in the DCN. This data supports that NAC/HPN-07 treatment reduces blast-induced TBI, including auditory centers such as the DCN and auditory cortex.

Example 4

The purpose of this example is to investigate the effect of HPN-07 and NAC on blood-brain barrier permeability Male Long-Evans pigmented rats (with body weights between 360 and 400 g, Harlan Laboratories, Indianapolis, Ind.) were injected intraperitoneally with a combination of 300 mg/kg of NAC plus 300 mg/kg of HPN-07, which were both dissolved in 5 ml/kg of physiological saline solution. Animals in the control group were injected i.p. with a similar volume of saline. Drug or saline was administered once on the first day and then twice a day for the following two days.

Seven days after the initial drug administration magnetic resonance imaging (MRI) was used to detect the disruption of the blood-brain barrier (BBB). Contrast enhancement noted on post-contrast T1-weighted MRI after injection of contrast agent (Magnevist=GdDTPA) is indicative of blood-brain barrier disruption. The hyperintensity on the T1-weighted images is resulting from leakage of the gadolinium based contrast agent injected at the baseline.

Figure 11:
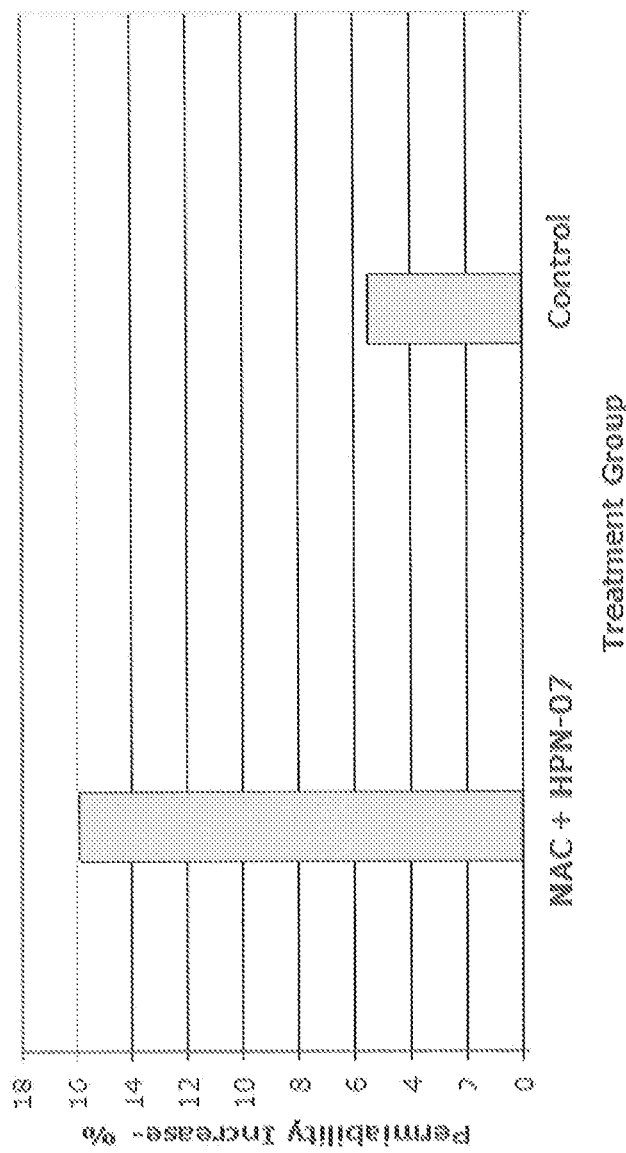
FIG. 11 provides a bar graph representing the percentage increase in blood-brain barrier permeability in subjects exposed to blast in the absence (control) and presence of 2,4-disulfonyl PBN (HPN-07)+NAC administered one hour post-blast.

Magnetic resonance images were obtained before and after injection of 0.4 mmol Gd/kg of Magnevist and demonstrated areas of disruption of the blood-brain barrier. The MRI parameters and image scale factor were kept constant for all T1-weighted images. The images were evaluated both visually and by region-of-interest (ROI) measurement. ROI measurements were obtained at the time points (before and after injection of contrast material on Ti-weighted images) brain. The difference in ROI signal intensity was normalized with respect to its value before injection of contrast material and reported as a % change as depicted in FIG. 11.

Since NAC is known to not increase blood-brain barrier permeability, these results were unexpected and indicate for the first time that HPN-07 effectively increases blood-brain barrier permeability thereby leading to increased bioavailability of any co-administered compound. Thus, the current invention also relates to a method for increasing blood brain permeability, where the method comprises administering 2,4-disulfonyl PBN to a patient in an amount sufficient to increase the permeability of the blood brain barrier and administering a second compound or substance, wherein the second compound or substance is being used to treat or diagnose a condition of the brain.

Example 5

The purpose of this example is to determine the long-term effects of 2,4-disulfonyl PBN in treating injury to the hippocampus and entorhinal cortex resulting from noise-induced TBI.

In this Example, three-5 year old chinchilla were freedom divided into 3 groups (6 chinchilla at each time point in each group). Chinchilla in noise exposure and noise plus treatment groups were exposed to 105 dB SPL Octave band noise centered at 4 kHz for 6 hours. Chinchilla in the noise plus treatment group were received HPN-07 treatment (300 mg/kg, i.p) started 4 hours after noise exposure, and then twice a day for the following 2 days. Chinchilla in the normal control and the noise exposed only groups were received carrier solutions (i.p.). Chinchilla were euthanized and perfused with 4% paraformaldehyde in PBS 21 days and 6 months after noise exposure. Brains were dissected out and post-fixed in the fixative for one week. The brains were Cryosected at 30 µm. Goat anti-doublecortin (1:100) was used to label neural precursor cells. Images were taken from CA1 regions of hippocampus and the entorhinal cortex with a light microscope. Doublecortin staining reflects neurogenerosis in the brain after neuron damage and death after noise exposure.

Figure 12A:
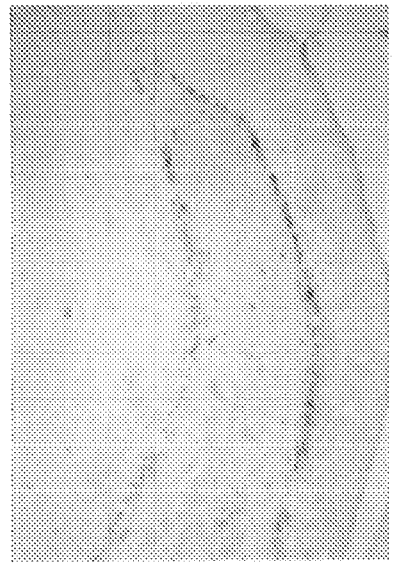
FIGS. 12A-12C represent doublecortin immunostained sections of the hippocampus in control subjects not exposed to noise trauma (FIG. 12A), subjects 6 months post noise exposure without treatment (FIG. 12B) and with HPN-07 treatment (FIG. 12C).
Figure 12B:
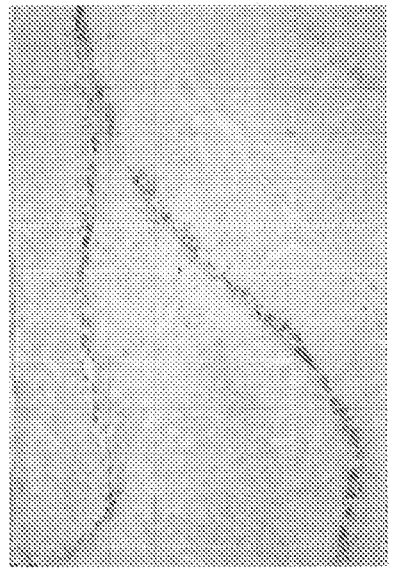
Figure 12C:

FIG. 12 represents doublecortin immunostained sections of the hippocampus in control subjects not exposed to noise (FIG. 12A), subjects 6 months post noise exposure without treatment (FIG. 12B) and with HPN-07 treatment (FIG. 12C). As demonstrated therein, the density of doublecortin staining is noticeably increased in the subjects exposed to noise compared to subjects treated with HPN-07 which display a doublecortin density comparable to the control subjects.

Similar results were obtained in the entorhinal cortex as depicted in FIG. 13. FIG. 13A shows very low levels of doublecortin staining in subjects under control conditions (not exposed to traumatic noise). FIGS. 13B and 13D demonstrates increased doublecortin staining 21 days and 6 months, respectively, following exposure to a traumatic noise event. FIGS. 13C and 13E demonstrate that treatment with HPN-07 decreases the level of doublecortin staining at both time points.

Taken together, these results suggest that noise exposure resulted in increased stem cell/repair activity in the hippocampus and entorhinal cortex that persists long after the traumatic event. Furthermore, the decreased repair activity in the subjects treated with HPN-07 suggests that this compound is effective to reduce the tissue injury caused by the traumatic noise event. The hippocampus plays important roles in the consolidation of information from short-term memory to long-term memory and spatial navigation, and the entorhinal cortex functions as a network hub for memory and navigation and also serves as the primary interface between the hippocampus and neocortex. Thus, these results also suggest that HPN-07 may be effective to treat noise induced long-term memory (LTM) deficits.

The examples demonstrates the effectiveness of 2,4-disulfonyl PBN, alone and in combination with NAC in treating noise-induced and blast-induced brain injury. In particular, the use of 2,4-disulfonyl PBN has been shown to reduce the cellular and molecular effects associated with secondary conditions resulting from traumatic brain injury. Finally, 2,4-disulfonyl PBN unexpectedly increases blood brain permeability which leads to increased bioavailability of the compound.

As used herein, a "pharmaceutically effective amount" is an amount of a pharmaceutical compound or composition having a therapeutically relevant effect on cellulalar damage or function, tissue damage or function, or other functional or physical symptoms resulting from traumatic brain injury including, but not limited to noise-induced tinnitus. A therapeutically relevant effect relates to some improvement in the physical or functional symptoms of traumatic brain injury or a change in the cellular, physiological, anatomical or biochemical markers associated with tramautic brain injury, including noise-induced and blast-induced brain injuries. In compositions comprising the combination of 2,4-disulfonyl PBN and NAC or 4-OHPBN and NAC and ALCAR, a pharmaceutically effective amount may be a dosage which is pharmaceutically effective for each compound, or in dosages which are sub-clinical for each compound, i.e., less than pharmaceutically effective for each individually, or a combination thereof, provided that the combined dosages are pharmaceutically effective.

In one embodiment, a method for treating traumatic brain injury or tinnitus comprises administering to an organism a pharmaceutically effective amount of a composition comprising 2,4-disulfonyl PBN and NAC. In one aspect, the composition comprises at least two parts NAC for every part of 2,4-disulfonyl PBN, i.e. a ratio of 2:1 to 2.5:1, NAC to 2,4-disulfonyl PBN. In another aspect, the composition comprises equal parts of 2,4-disulfonyl PBN and NAC. Furthermore, the concentration of NAC used in the composition of NAC with 2,4-disulfonyl PBN may be substantially less than treatment of a patient with NAC alone. The compositions may comprise between about 70 mg and about 1200 mg of 2,4-disulfonyl PBN and from about 700 mg and about 4000 mg of NAC. Furthermore, compositions comprising 2,4-disulfonyl PBN may be administered at a dose of between about 1 mg/kg to about 400 mg/kg body weight and more likely around 300 mg/kg body weight. Compositions comprising NAC may be administered at a dose of between about 5 mg/kg to about 300 mg/kg body weight. These ranges are based on the examples included herein and do not limit the range of pharmaceutically effective amounts for other organisms.

In another embodiment, a method for treating traumatic brain injury or tinnitus comprises administering to an organism a pharmaceutically effective amount of a composition comprising 4-OHPBN+NAC+ALCAR. Such composition can have a dose range between about 5 mg/kg and about 300 mg/kg for NAC, between about 5 mg/kg and about 150 mg/kg for 4-OHPBN and between about 5 mg/kg and about 500 mg/kg for ALCAR when ALCAR, NAC and 4-OHPBN are used in combination.

One skilled in the art from a reading of this disclosure will likely recognize related compounds which will also provide satisfactory results. Further, although the foregoing examples treated the test subjects one to four hours following noise exposure and blast exposure, treatments administered within shorter time periods should be as effective and will likely be preferred. In addition, treatments administered longer than 48 hour post noise exposure, blast exposure, stress or other cause of traumatic brain injury may also be effective. As such the foregoing disclosure is merely considered to be exemplary of the current invention with the true scope of the current invention being defined by the claims.

We claim:

1. A method for treating traumatic brain injury comprising: administering to a patient which has experienced a traumatic brain injury a pharmaceutically effective amount of a composition comprising 2,4-disulfonyl α-phenyl tertiary butyl nitrone and N-acetylcysteine.

2. The method of claim 1, wherein the brain injury is a closed brain injury.

3. The method of claim 2, wherein the closed brain injury is caused by exposure to noise.

4. The method of claim 2, wherein the closed brain injury is caused by exposure to a blast.

5. The method of claim 1, wherein the step of administering is oral.

6. The method of claim 1, wherein the composition is administered between one to four hours after the organism has experienced the traumatic brain injury.

7. The method of claim 1, wherein said composition further comprises one or more compounds selected from the group consisting of Acetyl-L-Carnitine, glutathione monoethylester, ebselen, D-methionine, carbamathione and Szeto-Schiller peptides.

8. A method for treating traumatic, closed brain injury comprising:
administering to a patient which has experienced a traumatic, closed brain injury caused by exposure to a blast or noise a pharmaceutically effective amount of a composition comprising 2,4-disulfonyl α-phenyl tertiary butyl nitrone.

9. The method of claim 8, wherein the step of administering is oral.

10. The method of claim 8, wherein the composition is administered between one to four hours after the organism has experienced the traumatic brain injury.

11. The method of claim 8, wherein said composition further comprises one or more compounds selected from the group consisting of N-acetylcysteine, Acetyl-L-Carnitine, glutathione monoethylester, ebselen, D-methionine, carbamathione and Szeto-Schiller peptides.

* * * * *